United States Patent
Smith et al.

(10) Patent No.: US 8,675,990 B2
(45) Date of Patent: Mar. 18, 2014

(54) COMPOSITE EVALUATION

(75) Inventors: Robert Alan Smith, Fleet (GB); Luke Joseph Nelson, Fleet (GB)

(73) Assignee: Qinetiq Limited, London (GB)

( * ) Notice: Subject to any disclaimer, the term of this patent is extended or adjusted under 35 U.S.C. 154(b) by 253 days.

(21) Appl. No.: 13/122,085

(22) PCT Filed: Oct. 2, 2009

(86) PCT No.: PCT/GB2009/002362
§ 371 (c)(1),
(2), (4) Date: May 12, 2011

(87) PCT Pub. No.: WO2010/038039
PCT Pub. Date: Apr. 8, 2010

(65) Prior Publication Data
US 2011/0274369 A1 Nov. 10, 2011

(30) Foreign Application Priority Data
Oct. 3, 2008 (GB) .................................. 0818088.7

(51) Int. Cl.
*G06K 9/36* (2006.01)
*G06K 9/40* (2006.01)

(52) U.S. Cl.
USPC .......................................... 382/280; 382/274

(58) Field of Classification Search
USPC ................. 382/276, 280, 307, 312, 128–134; 73/602
See application file for complete search history.

(56) References Cited

U.S. PATENT DOCUMENTS

| | | | |
|---|---|---|---|
| 5,277,761 A | | 1/1994 | Van Phan et al. |
| 5,390,544 A | * | 2/1995 | Madras ........................... 73/602 |
| 5,841,892 A | | 11/1998 | McGrath et al. |
| 7,320,241 B2 | * | 1/2008 | Kollgaard et al. ............. 73/1.86 |
| 8,210,045 B2 | * | 7/2012 | Caron ............................. 73/643 |
| 2005/0004956 A1 | | 1/2005 | Pourdeyhimi |

FOREIGN PATENT DOCUMENTS

WO WO 2007/024858 A1 3/2007

OTHER PUBLICATIONS

Hsu et al., "Ultrasonically Mapping the Ply Layup of Composite Laminates," Materials Evaluation, Sep. 2002, pp. 1099-1106.
Park et al., "On Feasibility of Ply-layup Orientation in CF/Epoxy Composite Laminates Using Rayleigh Probes," Advanced Materials Research, 2007, pp. 299-302, vols. 29-30.
British Search Report mailed Feb. 7, 2009 issued in British Patent Application No. 0818088.7.
International Search Report mailed Jul. 27, 2010 issued in International Patent Application No. PCT/GB2009/002362.
Written Opinion of the International Searching Authority mailed Jul. 27, 2010 issued in International Patent Application No. PCT/0132009/002362.

* cited by examiner

*Primary Examiner* — Kanjibhai Patel
(74) *Attorney, Agent, or Firm* — Oliff PLC

(57) ABSTRACT

A method of evaluating a composite structure in which a portion of the structure is imaged and subsequently transformed to provide a 2D output of the angular distribution of features, eg a 2D FFT. A weighting function is applied to the output to compensate for variation in the angular density of pixel population. The weighted output is then used to provide an angular distribution of feature intensity. The structure can be imaged in two or more intersecting planes to allow a 3D determination of feature direction to be obtained.

14 Claims, 6 Drawing Sheets

COMPOSITE EVALUATION

The present invention relates generally to evaluation of composite structures, and in particular to non-destructive evaluation using ultrasound techniques.

Composite materials are becoming increasingly widespread in their use, particularly in the aerospace industry. This rise in occurrence of composites has brought about the need for techniques for damage detection, characterisation and repair of composite structures. Until recently this need has been sufficiently small that it has been met by adapting methods designed for use with metals, or by attempting to extend techniques designed specifically for military purposes.

Pulse-echo ultrasonic scanning techniques have been developed to generate and measure the response of composite materials, exploiting the fact that ultrasound is reflected by acoustic impedance mismatches at boundaries between phases or materials of different composition. The measured responses can then be used to generate cross-sectional images through the composite, however such images can be difficult to interpret and reliably derive structural data from.

It is therefore an object of the present invention to provide improved methods of composite evaluation.

According to a first aspect of the invention there is provided a method of evaluating a composite structure comprising deriving an image of at least a portion of said structure, applying a transform to said image to derive a 2D output representing the angular distribution of features in said image, applying a weighting function to said 2D output to compensate for variation in pixel population density with angle, and deriving from said weighted 2D output an angular distribution of feature intensity.

It has been recognised by the present inventor that the pixel population density in the 2D output varies considerably with angle. Where relatively fine angular resolution is required, eg 0.25 degrees, certain angular ranges contain no pixels or data points. It has been found that this non-uniformity can lead to incomplete angular power distributions and hence reduced reliability. By applying a weighting function, pixels in the 2D output provide a contribution to the integral at more than one angle when determining the angular power distribution. This has the effect of rendering more complete and smoothing the distribution of contributions from 2D output pixels across the angular range.

As will be explained below, ultrasound images of composite structures can be derived which show tows of fibres as substantially parallel lines extending across an image. In such embodiments it is lines or edges in the image whose angular distributions are typically sought, and in one embodiment the transform is a spatial frequency transform, most commonly a 2D Discrete Fourier Transform (DFT) of Fast Fourier Transform (FFT). This results in the decomposition of the image into components of spatial frequency and angle.

In this way a discrete transform is applied to a periodic image of the composite having a number of discrete points in each dimension equal to a power of 2: $\{2^n | n=1, 2, 3, \ldots\}$. In order to achieve the correct number of points, mean padding is preferably applied by subtracting the mean value, windowing the data and padding with zeros to $2^n$ points. Subtracting the mean also removes the zero-frequency bright spot from the resulting 2D FFT and this is a considerable advantage for determining angular distributions. It is envisaged however that embodiments of some aspects of the invention may employ other transforms, such as a Z-transform, Wavelet Transform, Hough or Radon transform.

For some transforms, it is assumed that the image is periodic and that it is repeated by 'wrapping around' the image. To avoid discontinuities at the wrap-around, after subtracting the mean value, the image is multiplied by a tapered 'window' function in many embodiments, and various standard window functions such as a Hanning window, are suitable. The window function is preferably modified to apply the taper to just the edges of the selected region of the image. Embodiments which apply rectangular windowing are preferred, although circular windowing can have advantages for square images, such as the removal of bias in the angular power distribution.

The weighting function in many embodiments will be a Gaussian weighting function. However, other functions such as triangular, Hanning, reciprocal or parabolic are possible. The resultant effect is that a value at a given grid position in the 2D output provides a contribution across a broader range of angles. As such, the weighting function may also be embodied by mathematical equivalents, such as linear interpolation in polar coordinates.

The angular resolution of the distribution is preferably less than or equal to 1 degree, and more preferably less than or equal to 0.5 degree.

In a preferred embodiment the spread or angular width of the weighting function is inversely proportional to the spatial frequency in the 2D output. Alternatively or additionally the width of the weighting function can be adjusted to vary with angle, $\theta$. This is particularly useful in embodiments where the pixel aspect ratio in the 2D FFT output is not unity.

This evaluation can be repeated for images of further portions of the structure and the results may be stacked as a 3D distribution of dominant fibre orientation from each portion of structure. In general there would need to be at least three of these 3D distributions to describe the actual 3D fibre orientation in full—commonly known as azimuth (in-plane angle), pitch (out-of-plane angle viewed from a specified direction) and yaw (out-of-plane angle viewed from an orthogonal direction to the pitch). However, in some embodiments, two distributions of angle would suffice, eg azimuth and tilt (from the perpendicular axis in the direction of the azimuth angle).

Accordingly a further aspect of the invention provides a method of analysing a composite structure to provide data representative of the local dominant fibre orientation in three dimensions, said method comprising obtaining at least two substantially intersecting images of a portion of a structure in different planes; deriving an angular distribution of features of said images; and determining from said distributions a dominant 3D orientation angle.

The invention also provides a computer program and a computer program product for carrying out any of the methods described herein and/or for embodying any of the apparatus features described herein, and a computer readable medium having stored thereon a program for carrying out any of the methods described herein and/or for embodying any of the apparatus features described herein.

The invention extends to methods, apparatus and/or use substantially as herein described with reference to the accompanying drawings.

Any feature in one aspect of the invention may be applied to other aspects of the invention, in any appropriate combination. In particular, method aspects may be applied to apparatus aspects, and vice versa.

Furthermore, features implemented in hardware may generally be implemented in software, and vice versa. Any reference to software and hardware features herein should be construed accordingly.

DETAILED DESCRIPTION OF THE EMBODIMENTS

The mechanism of ultrasound reflection in carbon fibre composites allows the resin layer situated between two composite layers to be treated as a single interface for the purposes of this application, with the amplitude of the reflected signal varying substantially linearly with the resin thickness (subject to appropriate parameters). Resin layer thickness is in turn dependent upon the arrangement of fibres immediately above and below it, which generally are in 'tows' a few millimeters wide, causing ripples in the resin layer thickness. These ripples are detected as modulations in the reflected amplitude of ultrasound from the resin layer, and therefore ultrasound responses can be built up into images showing fibre orientation.

Three different types of ultrasound images are commonly referred to:

A-scan: Uses ultrasonic pulse-echo imaging technique at a point on the surface to create a 1D scan response through the composite at that point;

B-scan: Uses ultrasonic imaging along a line on the surface to obtain data at multiple depths at each point on that line, creating a 2D image of a vertical cross-section through the composite;

C-scan: Uses ultrasonic imaging over a 2D surface area to obtain data at each point on that surface creating images of a horizontal cross-section through the composite at a particular depth.

Figure 1A:
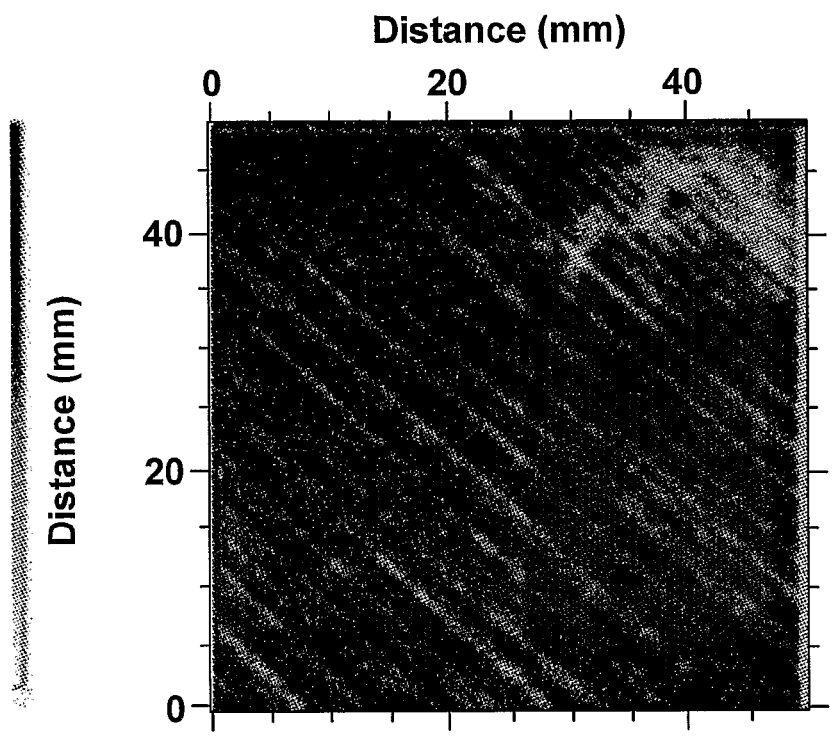
FIGS. 1a and 1b show ultrasound images of cross sections through a composite structure
Figure 1B:
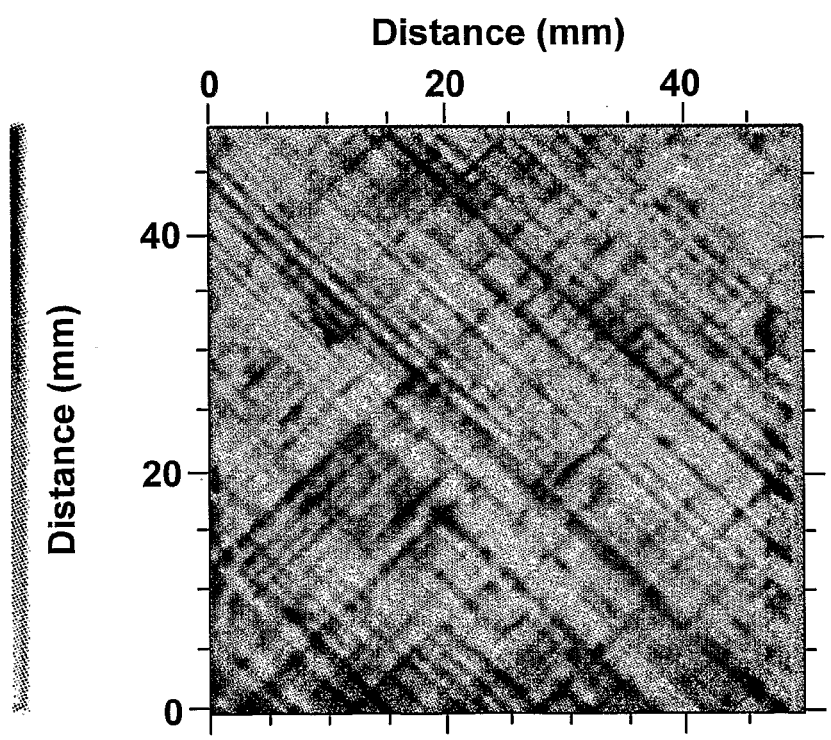

Two exemplary C-scans of a carbon fibre composite are shown in FIG. 1. In FIG. 1a the direction of the fibres can clearly be seen running from top left to bottom right. It must be remembered however that the C-scan of a ply interface generally shows lines in the direction of the fibre tows in the plies both above and below the interface (because both composite-to-resin boundaries reflect ultrasound and contribute to the overall reflection coefficient of that ply interface). This can be seen in FIG. 1b where both 135 degree and 45 degree orientations are visible.

Figure 2A:
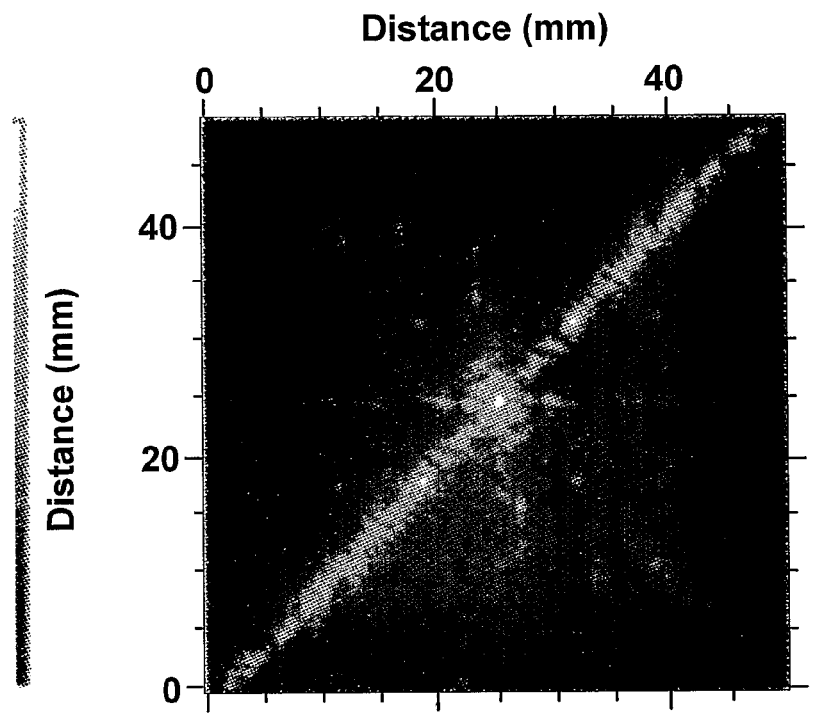
FIGS. 2a and 2b show the 2D FFT outputs of the images of FIG. 1
Figure 2B:
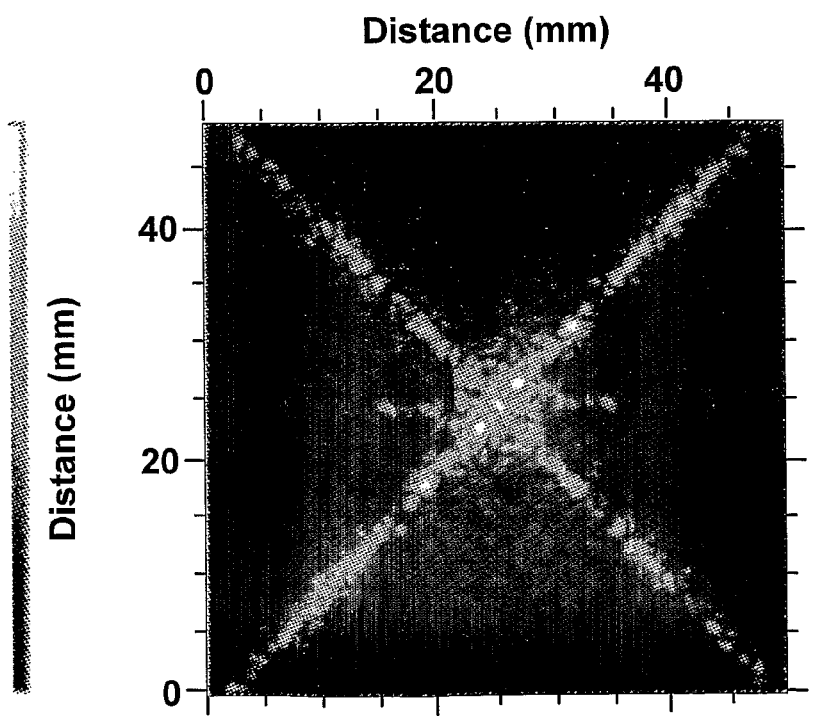

The C scans of FIG. 1 can be spatially decomposed by applying a 2D Fast Fourier Transform (FFT) to produce the 2D outputs shown in FIGS. 2a and 2b. The output of a 2D FFT is essentially a 2D matrix of discrete values. Each polar-coordinate position (v, θ) in the 2D output corresponds to a spatial frequency v at an orientation angle θ. The output image produced from an input C-scan image of a composite material contains information about the distribution of fibre orientations. The spatial frequency corresponds to how frequently you would encounter fibre tows if you were to travel over the image at an angle θ. The amplitude at each angle and spatial frequency can be plotted as a colour on a predefined colour scale (see FIG. 2). Other transforms produce 2D outputs where Cartesian coordinates represent the angle of a line or edge, and its distance from the image centre.

A Fast Fourier Transform (FFT) as described above works by applying a discrete Fourier transform to a periodic image that consists of a number of discrete points in each dimension equal to a power of 2: $\{2n|n=1, 2, 3, \ldots\}$. In the example of FIG. 1, the image is extended artificially to have 2n points by 'padding' it with points that take the mean value.

The majority of the energy in FIG. 2a, which corresponds to the output of a 2D FFT applied to FIG. 1a, can be seen to lie along the top-right to bottom-left diagonal of the 2D output, which is to be expected given the generally unidirectional nature of the input image. In FIG. 2b, which corresponds respectively with FIG. 1b, the energy can be seen to be distributed approximately equally between the two diagonal directions, reflecting the fact that the fibre tows can be observed running in two orthogonal directions in FIG. 1b. With the image data in the spatial frequency domain, it is also possible to apply a degree of high and/or low pass filtering to attenuate energy at spatial frequencies which are considered to be too far from the fibre tow spacing frequency.

Figure 3A:
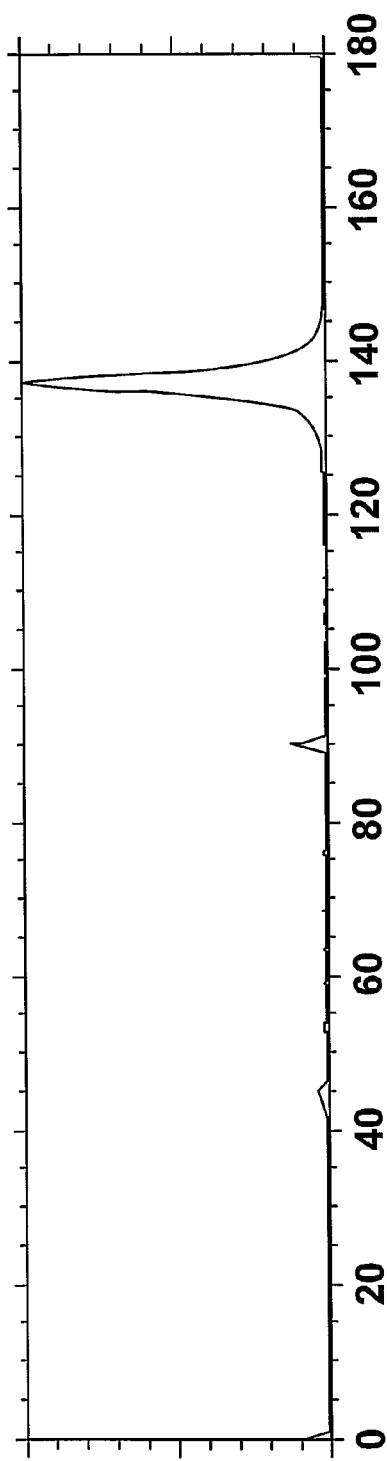
FIGS. 3a and 3b show the angular power distribution of the 2D outputs of FIG. 2
Figure 3B:
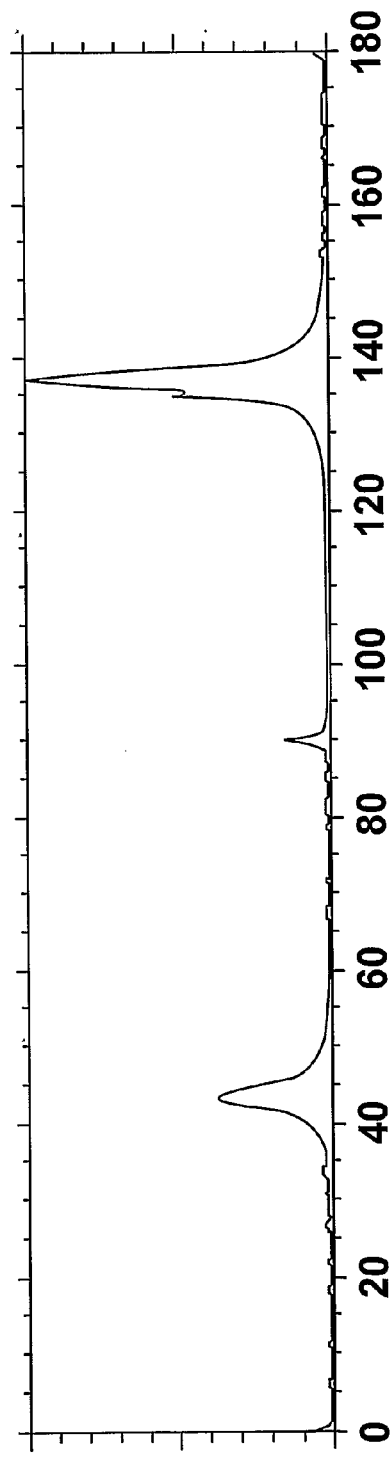

The qualitative information contained within the 2D FFT output and described above can be converted into a more readily useable form by producing an angular power distribution (APD) as shown in FIG. 3. The angular power distribution of FIGS. 1a and 2a is shown in FIG. 3a, and of FIGS. 1b and 2b, in 3b. The APD is a quantitative plot of intensity in the 2D image output of the FFT against orientation angle θ. The peak orientation angle or angles gives the dominant feature orientation, ie the fibre orientation in the image.

The angular power distribution is continuous with angle. This is unlike the 2D FFT output image, which is pixelated and so contains only the discrete values provided. As noted above however, pixel population density varies as a function of angle. Stated differently, a segment defined by a given angle will contain different numbers of pixels at different orientations. This is illustrated in FIG. 4.

Figure 4:
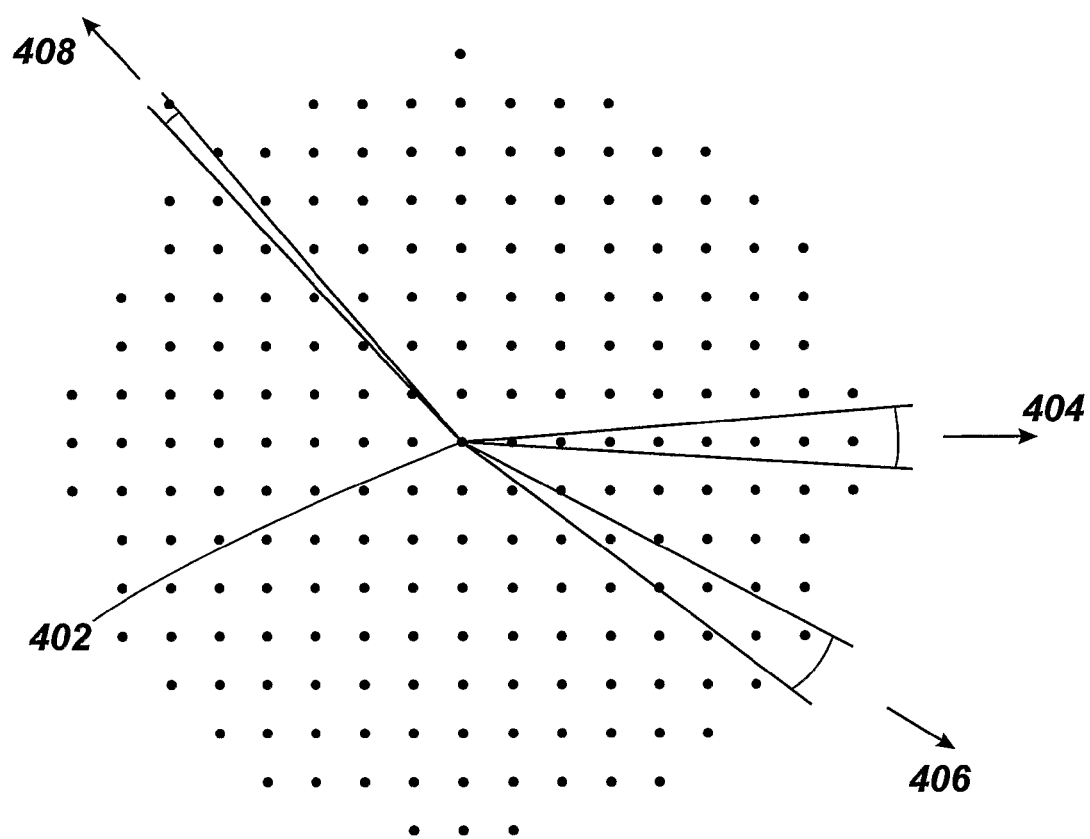
FIG. 4 illustrates pixel population distribution

In FIG. 4, the regular grid of points represents the array of values in the 2D FFT output. Central point 402 represents the zero spatial frequency in both horizontal and vertical directions. It can be seen that an arc segment taken along the 0 degree direction, indicated by arrow 404, will contain a large number of points because of the structure of the grid. An arc segment of the same angular size at a different orientation, indicated by arrow 406, will contain fewer points if it is misaligned with the regular grid spacing.

Segments along directions 404 and 406 illustrated in FIG. 4 have large angular values for ease of viewing, however in practical examples angles of a degree or of fractions of a degree are more commonly used. It will be understood that at such fine angular resolution, certain segments may contain no grid points. A smaller angular segment in direction 408 for example contains no grid points, while equally small segments which are aligned with the grid (eg 45, 90 degrees) will contain disproportionately higher numbers of points.

Figure 5:
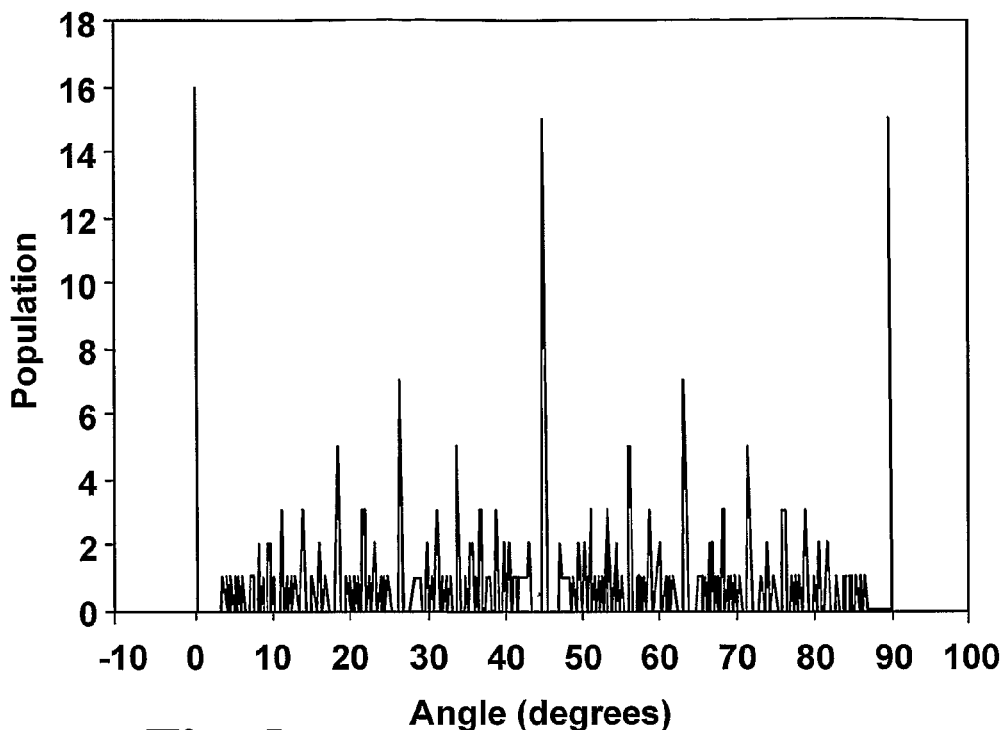
FIG. 5 is a graph of pixel population with angle for a given grid spacing

For an example grid of 16×16 points having unity aspect ratio and divided into 720 angular segments of 0.25 degrees, the population of points in each segment is shown in FIG. 5. The expected large peaks at 0, 45 and 90 are clearly visible, and it can also be seen that certain segments contain no points at all. This pixel population distribution tends to distort the angular power distribution because segments with zero populations cannot be corrected for this effect.

In order to account for any variations in population density as a function of angle, a weighting function is applied to each point in the 2D FFT output image. This weighting function has the effect of allocating a proportion of each pixel or point to the surrounding angles in order to avoid gaps in the angular distribution. A Gaussian weighting function is used in the present example to give a value for angular distribution $F(\theta)$:

$$F(\theta) = \frac{\sum_x \sum_y [a(x,y)]^2 e^{\frac{-[arctan(\frac{y}{x})-\theta]^2}{\varphi^2}}}{\sum_x \sum_y e^{\frac{-[arctan(\frac{y}{x})-\theta]^2}{\varphi^2}}}$$

Where:

x, y and a are the coordinates and value of each point in the 2D FFT

φ is the 1/e half-width of the Gaussian weighting

The value of the 1/e point on the Gaussian is an important consideration. Too large a value results in loss of angular resolution in the APD, while too low a value fails adequately to remove the effects of pixellation discussed above. A suitable method is to select φ in dependence upon the number of pixels in the 2D FFT. If a 2D FFT contains n×m points, then φ∝1/m·n. Alternatively φ can be modified in dependence upon the angle and/or spatial frequency of each point. In other words φ=f(arctan(y/x), √(x²+y²)).

The pixel aspect ratio is not unity in all cases. Where the pixel aspect ratio of the original scan image is not unity (eg because of the ultrasound sensing apparatus or method) then the 2D FFT output will typically have non-unity pixel aspect ratio. This further skews the pixel population distribution, either towards 0 degrees or towards 90 degrees depending on whether pixels are distorted in a landscape or portrait sense. In such cases it is particularly useful for the weighting function to be adjusted to vary with θ to compensate accordingly.

Figure 6:
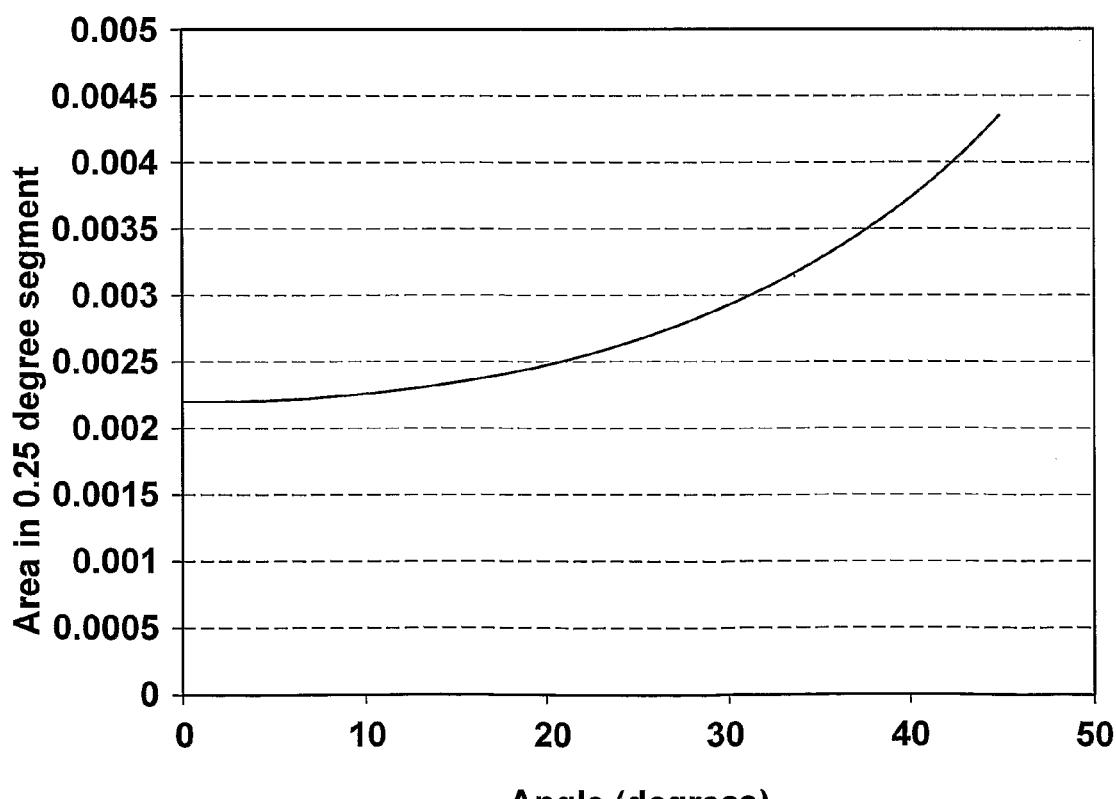
FIG. 6 is a graph of area compensation with angle.

In certain cases it is desirable to introduce a further correction to compensate for the variation in spatial frequency area with angular variation of each segment. This variation arises because the 2D FFT is not circular, typically being square, and therefore a 0.25 degree arc centred at 45 degrees will cover a larger area than an equivalent 0.25 degree arc at 0 or 90 degrees. The correction applied therefore varies as the segment angle increases from 0 to 45 degrees as shown in FIG. 6, with area A being given by:

$$A = \frac{\Delta \varphi}{2\cos^2 \varphi}$$

The methods described above allow an output of dominant fibre orientation in the plane of the original image to be produced. Where the image corresponds to a subset of the plane of the structure from which it is taken, the in-plane orientation is a local measure. It is therefore possible, by selecting a suitably sized window, and by scanning this window across the plane of the structure being evaluated, to draw up a 'map' of dominant in-plane fibre direction across the plane, providing data on the dominant direction at each location. For example 5 mm square windows can be employed with 50% overlap to provide data across the plane.

In the examples above, where C scans have been discussed, it is possible to analyse the same volume of a structure using B scans, to provide images in an orthogonal plane. Such images can be subject to the same or similar methods (the pixel aspect ratios of the two scan types may differ, and differing corrections may be applied appropriately, or not at all) to those described above to draw up data for the dominant fibre direction for each of a plurality of locations across the plane in question. By scanning a portion of composite structure to provide images in multiple orientations it is therefore possible to provide, for a plurality of sample points in three dimensions, the dominant fibre orientation, specified in three dimensions. In other words, where a fibre direction is known in a first given plane, by also assessing the fibre direction in a second different, intersecting plane, a complete measure of fibre direction including component both in and out of the first plane can be calculated. This is done by vector algebra and knowledge of the relationship between the frames of reference of the two measurement or imaging planes. Although preferred embodiments use orthogonal imaging planes, orthogonality is not required.

Figure 7:
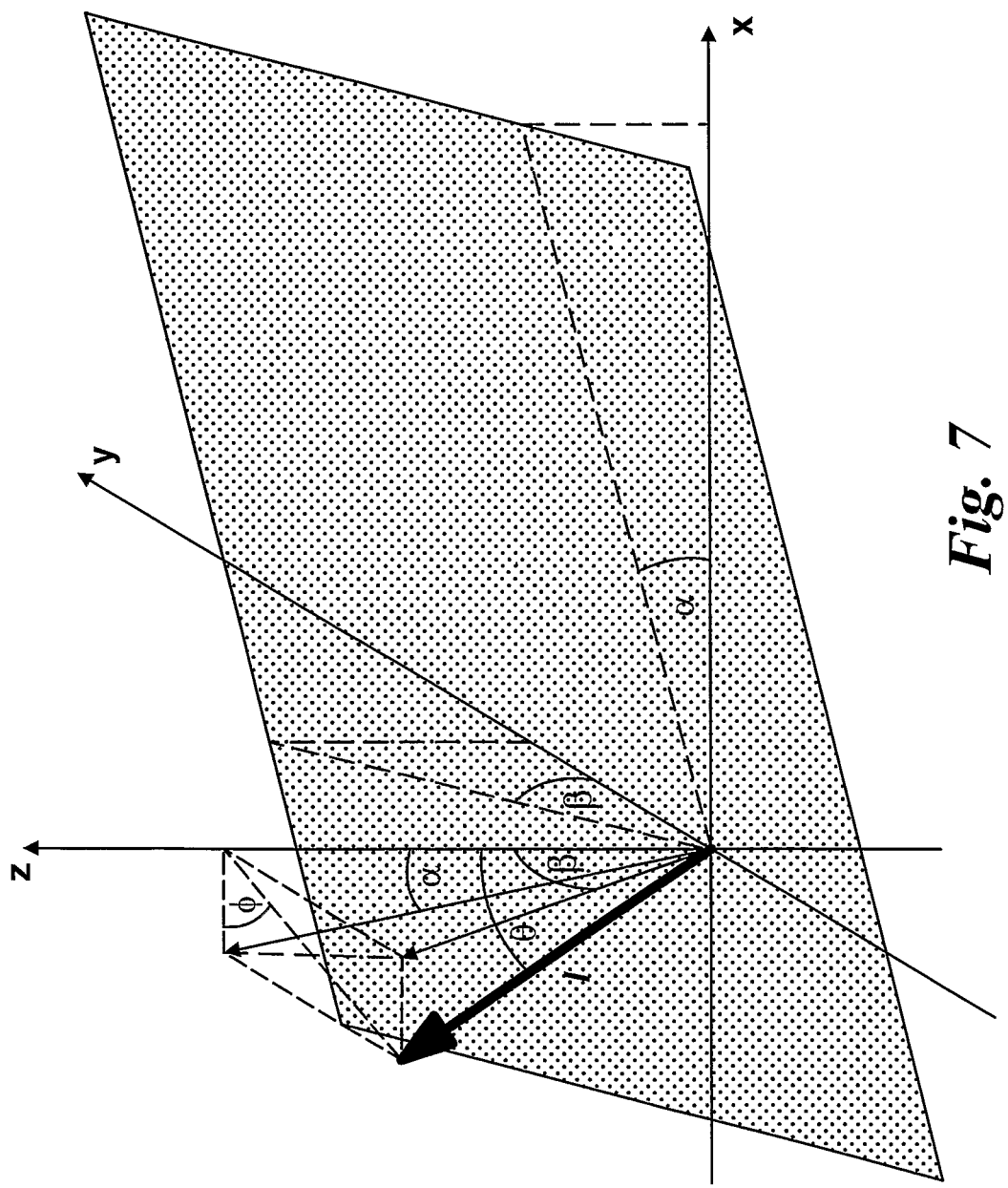
FIG. 7 illustrates ply angle and azimuthal direction calculations

FIG. 7 illustrates the calculation of peak angle and azimuthal direction coordinates by considering the unit vector perpendicular to the plane of the ply:

If I=(x,y,z) is the unit vector perpendicular to the inclined plane of the ply at the origin, then:

$x^2+y^2+z^2=1$ tan α=x/z tan β=y/z tan φ=y/x cos θ=z and from these equations, the following expressions can be derived:

tan φ=tan β/tan α tan² θ=tan² α+tan² β

In this example α and β can be determined by separate imaging in xz and yz planes respectively.

By providing a fibre direction information in a single 3D data set, alternative or additional test, verification and visualisation techniques can be employed, not previously available with one or more 2D in plane direction data sets.

It will be understood that the present invention has been described above purely by way of example, and modification of detail can be made within the scope of the invention. While an example of evaluation of a carbon fibre composite has been provided, the method is equally applicable to other composites such as metal matrix composites for example, and other inhomogeneous materials.

Each feature disclosed in the description, and (where appropriate) the claims and drawings may be provided independently or in any appropriate combination.

The invention claimed is:

1. A method of evaluating a composite structure comprising:
   using an ultrasonic imaging technique to perform the steps of:
   obtaining an image of at least a portion of said structure;
   applying a 2D FFT transform to said image to derive a 2D output representing an angular distribution of features in said image;
   applying a weighting function to said 2D output to compensate for variation in the angular density of pixel population; and
   deriving from said weighted 2D output an angular distribution of feature intensity.

2. A method according to claim 1, wherein the weighting function is a Gaussian.

3. A method according to claim 1, wherein the angular resolution of said distribution is less than 0.5 degree.

4. A method according to claim 1, wherein said 2D output is rectangular having m×n points.

5. A method according to claim 4, wherein an angular width of the weighting function is inversely proportional to m×n.

6. A method according to claim 1, wherein an angular width of the weighting function varies with spatial frequency.

7. A method according to claim 1, wherein an width of the weighting function varies with angle.

8. A method according to claim 1, wherein sample points of said 2D output have non-unity aspect ratio.

9. A method according to claim 1, wherein mean padding is applied to the image of said structure by subtracting mean value and padding to $(2)^n$ points with zeros.

10. A method according to claim 1, wherein said image is an ultrasonic B-scan.

11. A method according to claim 1, wherein said image is an ultrasonic C-scan.

12. A method according to claim 1 further deriving from said distribution a dominant orientation angle.

13. A method according to claim 1, further comprising applying a correction factor to said distribution to compensate for variation in output area with angular distribution.

14. A non-transitory computer readable medium having stored thereon computer implementable instructions for causing a programmable computer to perform a method according to claim 1.

* * * * *